United States Patent
Gordon et al.

(10) Patent No.: US 9,731,726 B2
(45) Date of Patent: Aug. 15, 2017

(54) REDIRECTING SELF-DRIVING VEHICLES TO A PRODUCT PROVIDER BASED ON PHYSIOLOGICAL STATES OF OCCUPANTS OF THE SELF-DRIVING VEHICLES

(71) Applicant: INTERNATIONAL BUSINESS MACHINES CORPORATION, Armonk, NY (US)

(72) Inventors: Michael S. Gordon, Yorktown Heights, NY (US); James R. Kozloski, New Fairfield, CT (US); Ashish Kundu, New York, NY (US); Peter K. Malkin, Ardsley, NY (US); Clifford A. Pickover, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 76 days.

(21) Appl. No.: 14/842,971

(22) Filed: Sep. 2, 2015

(65) Prior Publication Data

US 2017/0057516 A1    Mar. 2, 2017

(51) Int. Cl.
*G01C 22/00* (2006.01)
*G05D 1/00* (2006.01)
(Continued)

(52) U.S. Cl.
CPC .............. *B60W 40/08* (2013.01); *A61B 3/11* (2013.01); *A61B 5/0205* (2013.01);
(Continued)

(58) Field of Classification Search
CPC ......... B60W 40/08; B60W 2040/0818; B60W 2540/22; B60W 2600/00;
(Continued)

(56) References Cited

U.S. PATENT DOCUMENTS

| 4,908,988 A | 3/1990 | Yamamura et al. |
| 5,975,791 A | 11/1999 | McCulloch |

(Continued)

FOREIGN PATENT DOCUMENTS

| CN | 1135063 | 11/1996 |
| CN | 2349068 Y | 11/1999 |

(Continued)

OTHER PUBLICATIONS

U.S. Appl. No. 14/855,731 Non-final Office Action Mailed Apr. 15, 2016.

(Continued)

*Primary Examiner* — Jaime Figueroa
(74) *Attorney, Agent, or Firm* — Law Office of Jim Boice

(57) ABSTRACT

A computer-implemented method, system, and/or computer program product redirects a self-driving vehicle (SDV) to a physical location of a product provider. A self-driving vehicle (SDV) on-board computer on an SDV receives a current location and a planned route to an initial destination of the SDV. The SDV on-board computer receives information describing real-time physiological states of one or more occupants of the SDV, and then identifies a physical location of a product provider that provides a solution to ameliorate the real-time physiological states of the one or more occupants of the SDV. The SDV on-board computer then alters the planned route of the SDV to redirect the SDV on-board computer to autonomously drive the SDV to the physical location of the product provider.

17 Claims, 7 Drawing Sheets

(51) Int. Cl.
  *B60W 40/08* (2012.01)
  *A61B 5/0245* (2006.01)
  *A61B 5/053* (2006.01)
  *A61B 3/11* (2006.01)
  *A61B 5/0205* (2006.01)
  *A61B 5/16* (2006.01)
  *A61B 5/00* (2006.01)

(52) U.S. Cl.
  CPC .......... *A61B 5/0245* (2013.01); *A61B 5/0533* (2013.01); *A61B 5/165* (2013.01); *A61B 5/6893* (2013.01); *G05D 1/0061* (2013.01); *G05D 1/0088* (2013.01); *B60W 2040/0818* (2013.01); *B60W 2420/403* (2013.01); *B60W 2540/22* (2013.01); *B60W 2600/00* (2013.01)

(58) Field of Classification Search
  CPC .......... B60W 2420/403; A61B 5/0205; A61B 5/0245; A61B 5/0533; A61B 3/11; A61B 5/165; A61B 5/6893; G05D 1/0061; G05D 1/0088
  USPC ....................................................... 701/1, 28
  See application file for complete search history.

(56) References Cited

U.S. PATENT DOCUMENTS

| | | | |
|---|---|---|---|
| 6,064,970 A | 5/2000 | McMillan et al. | |
| 6,201,318 B1 | 3/2001 | Guillory | |
| 6,326,903 B1 | 12/2001 | Gross et al. | |
| 6,393,362 B1 | 5/2002 | Burns | |
| 6,502,035 B2 | 12/2002 | Levine | |
| 6,587,043 B1 | 7/2003 | Kramer | |
| 6,622,082 B1 | 9/2003 | Schmidt et al. | |
| 6,731,202 B1 | 5/2004 | Klaus | |
| 6,810,312 B2 | 10/2004 | Jammu et al. | |
| 7,124,088 B2 | 10/2006 | Bauer et al. | |
| 7,580,782 B2 | 8/2009 | Breed et al. | |
| 7,769,544 B2 | 8/2010 | Blesener et al. | |
| 7,877,269 B2 | 1/2011 | Bauer et al. | |
| 7,894,951 B2 | 2/2011 | Norris et al. | |
| 7,979,173 B2 | 7/2011 | Breed | |
| 8,031,062 B2 | 10/2011 | Smith | |
| 8,045,455 B1 | 10/2011 | Agronow et al. | |
| 8,078,349 B1 | 12/2011 | Prada Gomez et al. | |
| 8,090,598 B2 | 1/2012 | Bauer et al. | |
| 8,139,109 B2 | 3/2012 | Schmiedel et al. | |
| 8,140,358 B1 | 3/2012 | Ling et al. | |
| 8,146,703 B2 | 4/2012 | Baumann et al. | |
| 8,152,325 B2 | 4/2012 | McDermott | |
| 8,190,322 B2 | 5/2012 | Lin et al. | |
| 8,346,480 B2 | 1/2013 | Trepagnier et al. | |
| 8,352,112 B2 | 1/2013 | Mudalige | |
| 8,442,854 B2 | 5/2013 | Lawton et al. | |
| 8,466,807 B2 | 6/2013 | Mudalige | |
| 8,489,434 B1 | 7/2013 | Otis et al. | |
| 8,509,982 B2 | 8/2013 | Montemerlo et al. | |
| 8,583,365 B2 | 11/2013 | Jang et al. | |
| 8,660,734 B2 | 2/2014 | Zhu et al. | |
| 8,676,466 B2 | 3/2014 | Mudalige | |
| 8,786,461 B1 | 7/2014 | Daudelin | |
| 8,793,046 B2 | 7/2014 | Lombrozo et al. | |
| 8,816,857 B2 | 8/2014 | Nordin et al. | |
| 8,874,305 B2 | 10/2014 | Dolgov et al. | |
| 8,880,270 B1 | 11/2014 | Ferguson et al. | |
| 8,903,591 B1 | 12/2014 | Ferguson et al. | |
| 8,924,150 B2 | 12/2014 | Tsimhoni et al. | |
| 8,948,955 B2 | 2/2015 | Zhu et al. | |
| 8,949,016 B1 | 2/2015 | Ferguson et al. | |
| 8,954,217 B1 | 2/2015 | Montemerlo et al. | |
| 8,954,252 B1 | 2/2015 | Urmson et al. | |
| 8,954,261 B2 | 2/2015 | Das et al. | |
| 8,958,943 B2 | 2/2015 | Bertosa et al. | |
| 8,965,621 B1 | 2/2015 | Urmson et al. | |
| 8,970,362 B2 | 3/2015 | Morley et al. | |
| 8,996,224 B1 | 3/2015 | Herbach et al. | |
| 9,014,905 B1 | 4/2015 | Kretzschmar et al. | |
| 9,020,697 B2 | 4/2015 | Ricci et al. | |
| 9,024,787 B2 | 5/2015 | Alshinnawi et al. | |
| 9,082,239 B2 | 7/2015 | Ricci | |
| 9,123,049 B2 | 9/2015 | Hyde et al. | |
| 9,170,327 B2 | 10/2015 | Choe et al. | |
| 9,189,897 B1 | 11/2015 | Stenneth | |
| 9,194,168 B1 | 11/2015 | Lu et al. | |
| 9,216,745 B2 | 12/2015 | Beardsley et al. | |
| 9,286,520 B1 | 3/2016 | Lo et al. | |
| 9,305,411 B2 | 4/2016 | Ricci | |
| 9,317,033 B2 | 4/2016 | Ibanez-Guzman et al. | |
| 9,390,451 B1 | 7/2016 | Slusar | |
| 9,399,472 B2 | 7/2016 | Minoiu-Enache | |
| 9,463,805 B2 * | 10/2016 | Kirsch .................. | B60W 40/08 |
| 9,483,948 B1 | 11/2016 | Gordon et al. | |
| 2002/0026841 A1 | 3/2002 | Svendsen | |
| 2003/0065572 A1 | 4/2003 | McNee et al. | |
| 2003/0076981 A1 | 4/2003 | Smith et al. | |
| 2004/0078133 A1 | 4/2004 | Miller | |
| 2004/0199306 A1 | 10/2004 | Heilmann et al. | |
| 2005/0104745 A1 | 5/2005 | Bachelder et al. | |
| 2006/0106671 A1 | 5/2006 | Biet | |
| 2006/0163939 A1 | 7/2006 | Yuramochi et al. | |
| 2006/0200379 A1 | 9/2006 | Biet | |
| 2006/0241855 A1 | 10/2006 | Joe et al. | |
| 2007/0100687 A1 | 5/2007 | Yoshikawa | |
| 2007/0124027 A1 | 5/2007 | Betzitza et al. | |
| 2008/0048850 A1 | 2/2008 | Yamada | |
| 2008/0114663 A1 | 5/2008 | Watkins et al. | |
| 2008/0129475 A1 * | 6/2008 | Breed .................... | G07C 5/008 340/438 |
| 2008/0201217 A1 | 8/2008 | Bader et al. | |
| 2009/0094109 A1 | 4/2009 | Aaronson et al. | |
| 2009/0248231 A1 | 10/2009 | Kamiya | |
| 2009/0313096 A1 | 12/2009 | Kaga | |
| 2010/0057511 A1 | 3/2010 | Mansouri et al. | |
| 2010/0156672 A1 | 6/2010 | Yoo et al. | |
| 2010/0179720 A1 | 7/2010 | Lin et al. | |
| 2010/0228427 A1 | 9/2010 | Anderson et al. | |
| 2010/0256852 A1 | 10/2010 | Mudalige | |
| 2011/0035250 A1 | 2/2011 | Finucan | |
| 2011/0077807 A1 | 3/2011 | Hyde et al. | |
| 2011/0137699 A1 | 6/2011 | Ben-Ari et al. | |
| 2011/0264521 A1 | 10/2011 | Straka | |
| 2012/0277947 A1 | 11/2012 | Boehringer et al. | |
| 2013/0030657 A1 | 1/2013 | Chatterjee et al. | |
| 2013/0113634 A1 | 5/2013 | Hutchinson et al. | |
| 2013/0131949 A1 | 5/2013 | Shida | |
| 2013/0144502 A1 | 6/2013 | Shida | |
| 2013/0231824 A1 | 9/2013 | Wilson et al. | |
| 2013/0261871 A1 | 10/2013 | Hobbs et al. | |
| 2014/0019259 A1 | 1/2014 | Dung et al. | |
| 2014/0092332 A1 | 4/2014 | Price | |
| 2014/0095214 A1 | 4/2014 | Mathe et al. | |
| 2014/0129073 A1 | 5/2014 | Ferguson | |
| 2014/0136045 A1 | 5/2014 | Zhu et al. | |
| 2014/0136414 A1 | 5/2014 | Abhyanker | |
| 2014/0164126 A1 | 6/2014 | Nicholas et al. | |
| 2014/0188999 A1 | 7/2014 | Leonard et al. | |
| 2014/0195213 A1 | 7/2014 | Kozloski | |
| 2014/0201037 A1 | 7/2014 | Mallawarachchi et al. | |
| 2014/0201126 A1 | 7/2014 | Zadeh | |
| 2014/0214255 A1 | 7/2014 | Dolgov et al. | |
| 2014/0222277 A1 | 8/2014 | Tsimhoni et al. | |
| 2014/0222577 A1 | 8/2014 | Abhyanker | |
| 2014/0282967 A1 | 9/2014 | Maguire | |
| 2014/0297116 A1 | 10/2014 | Anderson et al. | |
| 2014/0306833 A1 * | 10/2014 | Ricci .................... | B60Q 1/00 340/901 |
| 2014/0309789 A1 * | 10/2014 | Ricci .................... | B60Q 1/00 700/276 |
| 2014/0309806 A1 * | 10/2014 | Ricci .................... | B60Q 1/00 701/1 |
| 2014/0309864 A1 * | 10/2014 | Ricci .................... | H04W 48/04 701/36 |

(56) References Cited

U.S. PATENT DOCUMENTS

| | | | |
|---|---|---|---|
| 2014/0309891 A1* | 10/2014 | Ricci | H04W 48/04 |
| | | | 701/48 |
| 2014/0310186 A1 | 10/2014 | Ricci | |
| 2014/0316671 A1 | 10/2014 | Okamoto | |
| 2014/0324268 A1 | 10/2014 | Montemerlo et al. | |
| 2014/0330479 A1 | 11/2014 | Dolgov | |
| 2014/0358331 A1 | 12/2014 | Prada Gomez et al. | |
| 2014/0358353 A1 | 12/2014 | Ibanez-Guzman et al. | |
| 2015/0006005 A1 | 1/2015 | Yu et al. | |
| 2015/0006014 A1 | 1/2015 | Wimmer et al. | |
| 2015/0026092 A1 | 1/2015 | Abboud et al. | |
| 2015/0035685 A1 | 2/2015 | Strickland et al. | |
| 2015/0051778 A1 | 2/2015 | Mueller | |
| 2015/0057891 A1 | 2/2015 | Mudalige et al. | |
| 2015/0062340 A1 | 3/2015 | Datta et al. | |
| 2015/0062469 A1 | 3/2015 | Fleury | |
| 2015/0066282 A1 | 3/2015 | Yopp | |
| 2015/0066284 A1 | 3/2015 | Yopp | |
| 2015/0070178 A1 | 3/2015 | Kline | |
| 2015/0095190 A1 | 4/2015 | Hammad et al. | |
| 2015/0134178 A1 | 5/2015 | Minoiu-Enache | |
| 2015/0141043 A1 | 5/2015 | Abramson | |
| 2015/0149021 A1 | 5/2015 | Duncan et al. | |
| 2015/0160019 A1 | 6/2015 | Biswal et al. | |
| 2015/0166059 A1 | 6/2015 | Ko | |
| 2015/0175070 A1 | 6/2015 | Attard et al. | |
| 2015/0178998 A1 | 6/2015 | Attard et al. | |
| 2015/0196256 A1 | 7/2015 | Venkatraman et al. | |
| 2015/0232065 A1* | 8/2015 | Ricci | B60R 25/01 |
| | | | 701/36 |
| 2015/0293994 A1 | 10/2015 | Kelly | |
| 2015/0338226 A1 | 11/2015 | Mason et al. | |
| 2015/0339639 A1 | 11/2015 | Choe | |
| 2016/0001781 A1* | 1/2016 | Fung | G06F 19/345 |
| | | | 701/36 |
| 2016/0026182 A1 | 1/2016 | Boroditsky et al. | |
| 2016/0075512 A1 | 3/2016 | Lert, Jr. | |
| 2016/0078695 A1 | 3/2016 | Mcclintic et al. | |
| 2016/0078758 A1 | 3/2016 | Basalamah | |
| 2016/0139594 A1 | 5/2016 | Okumura et al. | |
| 2016/0140507 A1 | 5/2016 | Stevens et al. | |
| 2016/0176409 A1* | 6/2016 | Kirsch | B60W 40/08 |
| | | | 701/37 |
| 2016/0303969 A1* | 10/2016 | Akula | B60K 35/00 |
| 2016/0334797 A1 | 11/2016 | Ross et al. | |
| 2016/0344737 A1 | 11/2016 | Anton | |
| 2016/0355192 A1 | 12/2016 | James et al. | |
| 2016/0364823 A1 | 12/2016 | Cao | |

FOREIGN PATENT DOCUMENTS

| | | |
|---|---|---|
| CN | 201004265 Y | 1/2008 |
| CN | 202012052 | 10/2011 |
| CN | 202038228 U | 11/2011 |
| CN | 102650882 | 8/2012 |
| CN | 202772924 | 3/2013 |
| CN | 104900018 A | 9/2015 |
| EP | 0582236 A1 | 2/1994 |
| WO | 2014058263 A1 | 4/2014 |
| WO | 2014066721 A2 | 5/2014 |
| WO | 2014147361 A1 | 9/2014 |
| WO | 2014148975 A1 | 9/2014 |
| WO | 2014148976 A1 | 9/2014 |
| WO | 2015024616 A1 | 2/2015 |
| WO | 2015056105 A1 | 4/2015 |
| WO | 2015156146 A1 | 10/2015 |

OTHER PUBLICATIONS

P. Mell et al., "The NIST Definition of Cloud Computing", National Institute of Standards and Technology, Information Technology Laboratory, Sep. 2011, pp. 1-7.

X. Jardin, "Terrifying dashcam video captures distracted teen drivers crashing while goofing off", Boing Boing, www.boingboing.net, Mar. 26, 2015, 1 page.

M. Fox, "Self-driving cars safer than those driven by humans: Bob Lutz", CNBC, www.cnbc.com, Sep. 8, 2014, 1 page.

Anonymous, "System and Method to Target Advertisements for the Right Focus Group", IP.com, No. 000218285, May 31, 2012, pp. 1-2.

U.S. Appl. No. 14/887,388, filed Oct. 20, 2015.

A. Abkowitz, "Do Self-Driving Cars Spell Doom for Auto Insurers?", Bloomberg L.P., Sep. 10, 2014, pp. 1-2.

Anonymous, "Self-Driving Cars and Insurance", Insurance Information Institute, Inc., Feb. 2015, pp. 1-3.

Gomes, Lee. "Google's Self-Driving Cars Still Face Many Obstacles / MIT Technology Review.", MIT Technology Review. Aug. 28, 2014. Web. <http://www.technologyreview.co,/news/530276/hidden-obstabscles-for-googles-self-driving-cars/>.

Smith, Mark. "Inovations: Emerging Trends in the Wheelchair Market." New Mobility Magazine, Aug. 1, 2014. Web. <http://www.newmobility.com/2014/08/emerging-trends/>.

Crothers, Brooke. "Google Now Reporting Self-Driving Car Accidents: Her, It's Not the Car's Fault". forbes.com, Jun. 8, 2015. <http://www.forbes.com/sites/brookecrothers/2015/06/08/google-now-reportibg-driverless-car-accidents/>.

E. Lehrer, "The Insurance Implications of Google's Self-Driving Car", Insurance Journal, Right Street Bloh=G, May 28, 2014, pp. 1-2.

Anonymous, "Car Built-In Mechanism to Enforce Mandatory Self-Driving Mode", ip.com, No. 000234916, Feb. 14, 2014, pp. 1-3.

T. Horberry et al., "Driver Distraction: The Effects of Concurrent In-Vehicle Tasks, Road Enviornment Complexity and Age on Driving Performance", Elsevier Ltd., Accident Analysis and Prevention, 38, 2006, pp. 185-191.

J. Miller, "Self-Driving Car Technologu's Benefits, Potential Risks, and Solutions", The Energy Collective, theenergycollective.com, Aug. 19, 2014, pp. 1-7.

J. O'Callaghan, "Inside the Mercedes Self-Guidubg Car That's Built for Luxurious Living in, Not Driving", Associated Newspapers Ltd., Daily Mail, dailymail.com.uk, Jan. 6, 2015, pp. 1-13.

J. Wei et al., "Towards a Viable Autonomous Driving Research Platform", IEEE, Intelegent Vehicles Symposium (IV), 2013, pp. 1-8.

J. Farrier, "Airlines Infuse Their Planes With Smells to Calm You Down", Neatorama, neatorama.com, Mar. 29, 2015, 1 Page.

T. Vanderbilt, "Let the Robot Drive: The Autonomous Car of the Future Is Here", Wired Magazine, Conde Nast, www.wired.com, Jan. 20, 2012. pp. 1-34.

Chen S, et al., A Crash Risk Assessment Model for Roas Curves. Inproceedings 20th International Technical Conference on the Enhanced Saftey of Vehicles., 2007. Lyon, France.

Anonymous, "Diagnostics Mechanism for Self-Driving Cars to Validate Self-Driving Capabilities", ip.com, Jun. 6, 2014, pp. 1-5. ip.com.

Brownell, "Shared Autonomous Taxi Networks: An Analysis of Transportation Demand in NJ and a 21st Century Solution for Congestion", Dissertation, Princeton University, 2013, pp. 1-122.

Sessa et al., "Blueprint of Alternative City Cyber-Mobility Take-U Scenarios", Seventh Framework Programme Theme SST.2012.3.1-4, Automated Urban Vehicles Collaborative Project—Grant Agreement No. 314190, 2013, pp. 1-63.

Lutin et al., "The Revolutionary Development of Self-Driving Vehicles and Implications for the Transportation Engineering Profession", ITE Journal 83.7, 2013, pp. 28-32.

A. Hars, "Self-Driving Cars: The Digital Transformation of Mobility", Marktplatze Im Umbruch, Springer Berlin Heidelberg, 2015, pp. 539-549.

Jimenez et al.; "Autonomous collision avoidance system based on accurate knowledge of the vehicle surroundings"; Inst Engineering Technology—IET; IET Intelligent Transport Systems vol. 9, No. 1, pp. 105-117; 2015; England.

Anonymous, "Avoiding Crashes With Self-Driving Cars: Today's Crash-Avoidance Systems are the Mile Markers to Tomorrow's Autonomous Vehicles". Consumer Reports Magazine, Feb. 2014.

(56) References Cited

OTHER PUBLICATIONS

Web. Sep. 22, 2016. <http://www.consumerreports.org/cro/magazine/2014/04/the-road-to-self-driving-cars/index.htm>.

Anonymous, "Google Files Patent for Second-Gen Autonomous Vehicle Without a Steering Wheel, Brake Pedal & More". patentlymobile.com, Nov. 27, 2015. Web. Sep. 22, 2016. <http://www.patentlymobile.com/2015/11/google-files-patent-for-second-gen-autonomous-vehicle-without-a-steering-wheel-brake-pedal-more.html>.

C. Berger et al., "COTS-Architecture With a Real-Time OS for a Self-Driving Miniature Vehicle", Safecomp 2013—Workshop ASCOMS of the 32nd International Conference on Computer Safety, Reliability and Security, Sep. 2013, Toulouse, France, pp. 1-13.

* cited by examiner

REDIRECTING SELF-DRIVING VEHICLES TO A PRODUCT PROVIDER BASED ON PHYSIOLOGICAL STATES OF OCCUPANTS OF THE SELF-DRIVING VEHICLES

BACKGROUND

The present disclosure relates to the field of vehicles, and specifically to the field of self-driving vehicles. Still more specifically, the present disclosure relates to the field of automatically driving self-driving vehicles to a product provider based on current physiological states of occupants of the self-driving vehicles.

Self-driving vehicles (SDVs) are vehicles that are able to autonomously drive themselves through private and/or public spaces. Using a system of sensors that detect the location and/or surroundings of the SDV, logic within or associated with the SDV controls the propulsion, stopping, and steering of the SDV based on the sensor-detected location and surroundings of the SDV.

SUMMARY

A computer-implemented method, system, and/or computer program product redirects a self-driving vehicle (SDV) to a physical location of a product provider. A self-driving vehicle (SDV) on-board computer on an SDV receives a current location and a planned route to an initial destination of the SDV. The SDV on-board computer receives information describing real-time physiological states of one or more occupants of the SDV, and then identifies a physical location of a product provider that provides a solution to ameliorate the real-time physiological states of the one or more occupants of the SDV. The SDV on-board computer then alters the planned route of the SDV to redirect the SDV on-board computer to autonomously drive the SDV to the physical location of the product provider.

DETAILED DESCRIPTION

Figure 1:
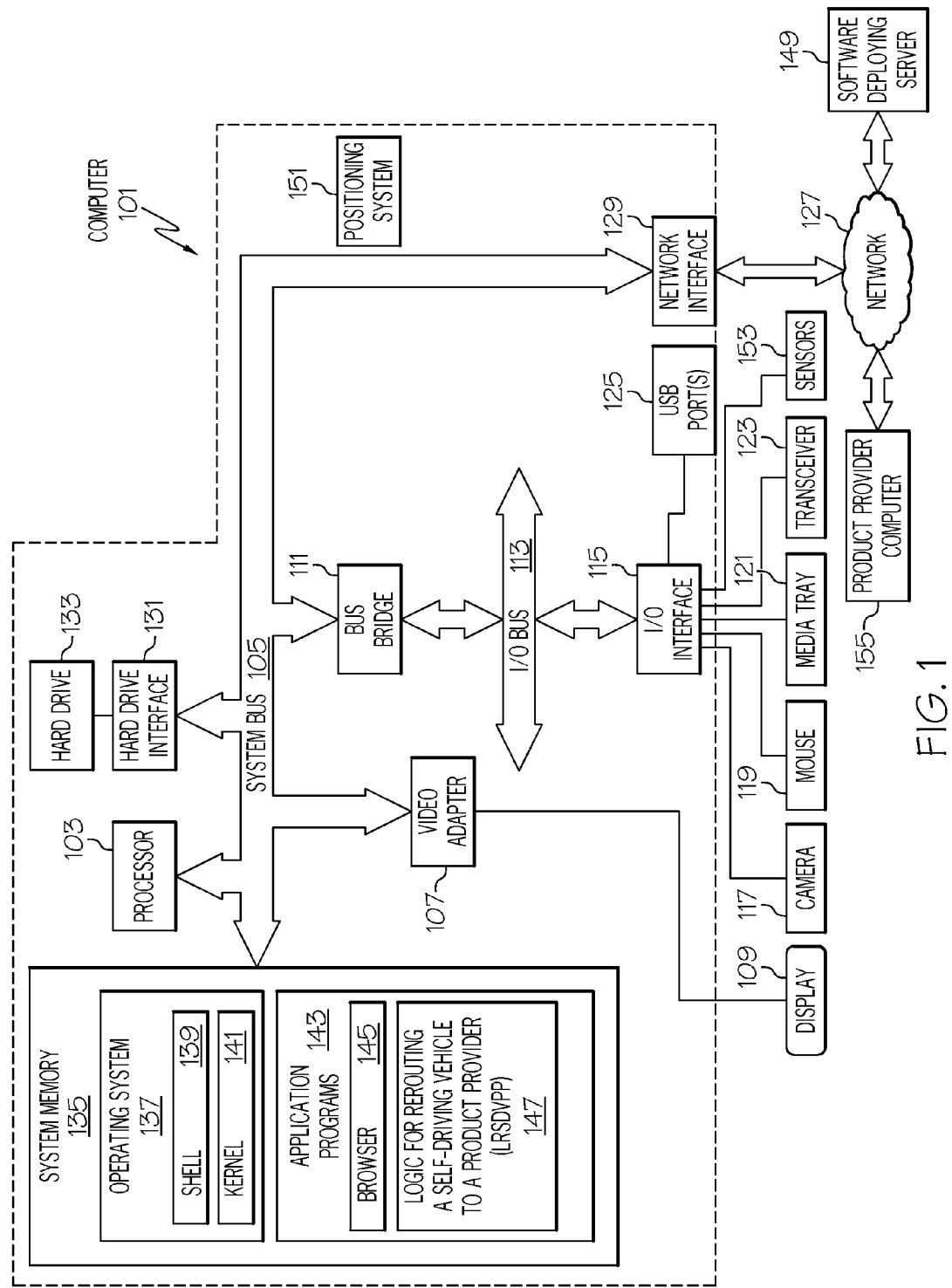
FIG. 1 depicts an exemplary system and network in which the present disclosure may be implemented.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Product provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

With reference now to the figures, and in particular to FIG. 1, there is depicted a block diagram of an exemplary system and network that may be utilized by and/or in the implementation of the present invention. Some or all of the exemplary architecture, including both depicted hardware and software, shown for and within computer 101 may be utilized by software deploying server 149 and/or a product provider computer 155 shown in FIG. 1, and/or a self-driving vehicle (SDV) on-board computer 301 shown in FIG. 3.

Exemplary computer 101 includes a processor 103 that is coupled to a system bus 105. Processor 103 may utilize one or more processors, each of which has one or more processor cores. A video adapter 107, which drives/supports a display 109, is also coupled to system bus 105. System bus 105 is coupled via a bus bridge 111 to an input/output (I/O) bus 113. An I/O interface 115 is coupled to I/O bus 113. I/O interface 115 affords communication with various I/O devices, including a camera 117 (e.g., a digital camera that is capable of capturing still and/or moving images), a mouse 119, a media tray 121 (which may include storage devices such as CD-ROM drives, multi-media interfaces, etc.), a transceiver 123 (capable of transmitting and/or receiving electronic communication signals), and external USB port(s) 125. While the format of the ports connected to I/O interface 115 may be any known to those skilled in the art of computer architecture, in one embodiment some or all of these ports are universal serial bus (USB) ports.

As depicted, computer 101 is able to communicate with a software deploying server 149 and/or other devices/systems (e.g., product provider computer 155) using a network interface 129. Network interface 129 is a hardware network interface, such as a network interface card (NIC), etc. Network 127 may be an external network such as the Internet, or an internal network such as an Ethernet or a virtual private network (VPN). In one or more embodiments, network 127 is a wireless network, such as a Wi-Fi network, a cellular network, etc.

A hard drive interface 131 is also coupled to system bus 105. Hard drive interface 131 interfaces with a hard drive 133. In one embodiment, hard drive 133 populates a system memory 135, which is also coupled to system bus 105. System memory is defined as a lowest level of volatile memory in computer 101. This volatile memory includes additional higher levels of volatile memory (not shown), including, but not limited to, cache memory, registers and buffers. Data that populates system memory 135 includes computer 101's operating system (OS) 137 and application programs 143.

OS 137 includes a shell 139, for providing transparent user access to resources such as application programs 143. Generally, shell 139 is a program that provides an interpreter and an interface between the user and the operating system. More specifically, shell 139 executes commands that are entered into a command line user interface or from a file. Thus, shell 139, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 141) for processing. While shell 139 is a text-based, line-oriented user interface, the present invention will equally well support other user interface modes, such as graphical, voice, gestural, etc.

As depicted, OS 137 also includes kernel 141, which includes lower levels of functionality for OS 137, including providing essential services required by other parts of OS 137 and application programs 143, including memory management, process and task management, disk management, and mouse and keyboard management.

Application programs 143 include a renderer, shown in exemplary manner as a browser 145. Browser 145 includes program modules and instructions enabling a world wide web (WWW) client (i.e., computer 101) to send and receive network messages to the Internet using hypertext transfer protocol (HTTP) messaging, thus enabling communication with software deploying server 149 and other systems.

Application programs 143 in computer 101's system memory (as well as software deploying server 149's system memory) also include Logic for Rerouting a Self-Driving Vehicle to a Product Provider (LRSDVPP) 147. LRSDVPP 147 includes code for implementing the processes described below, including those described in FIGS. 2-5. In one embodiment, computer 101 is able to download LRSDVPP 147 from software deploying server 149, including in an on-demand basis, wherein the code in LRSDVPP 147 is not downloaded until needed for execution. In one embodiment of the present invention, software deploying server 149 performs all of the functions associated with the present invention (including execution of LRSDVPP 147), thus freeing computer 101 from having to use its own internal computing resources to execute LRSDVPP 147.

Also within computer 101 is a positioning system 151, which determines a real-time current location of computer 101 (particularly when part of an emergency vehicle and/or a self-driving vehicle as described herein). Positioning system 151 may be a combination of accelerometers, speedometers, etc., or it may be a global positioning system (GPS) that utilizes space-based satellites to provide triangulated signals used to determine two or three dimensional locations.

Also associated with computer 101 are sensors 153, which detect an environment of the computer 101. More specifically, sensors 153 are able to detect other vehicles, road obstructions, pedestrians, construction sites, etc. For example, if computer 101 is on board a self-driving vehicle (SDV), then sensors 153 may be cameras, radar transceivers, microphones, etc. that allow the SDV to detect the environment (e.g., other vehicles, road obstructions, pedestrians, etc.) of that SDV.

Furthermore, sensors 153 may be sensors that detect biometric or other physiological states of occupants of an SDV. For example, sensors 153 may be remote sensors that are able to detect pupil dilation, galvanic skin responses (e.g., skin resistance changes caused by sweating), blood pressure and electrocardiogram sensors (e.g., blood pressure monitors attached to one or more persons), etc. that detect and quantify/qualify the physiological condition of one or more occupants of the SDV.

The hardware elements depicted in computer 101 are not intended to be exhaustive, but rather are representative to highlight essential components required by the present invention. For instance, computer 101 may include alternate memory storage devices such as magnetic cassettes, digital versatile disks (DVDs), Bernoulli cartridges, and the like. These and other variations are intended to be within the spirit and scope of the present invention.

Figure 2:
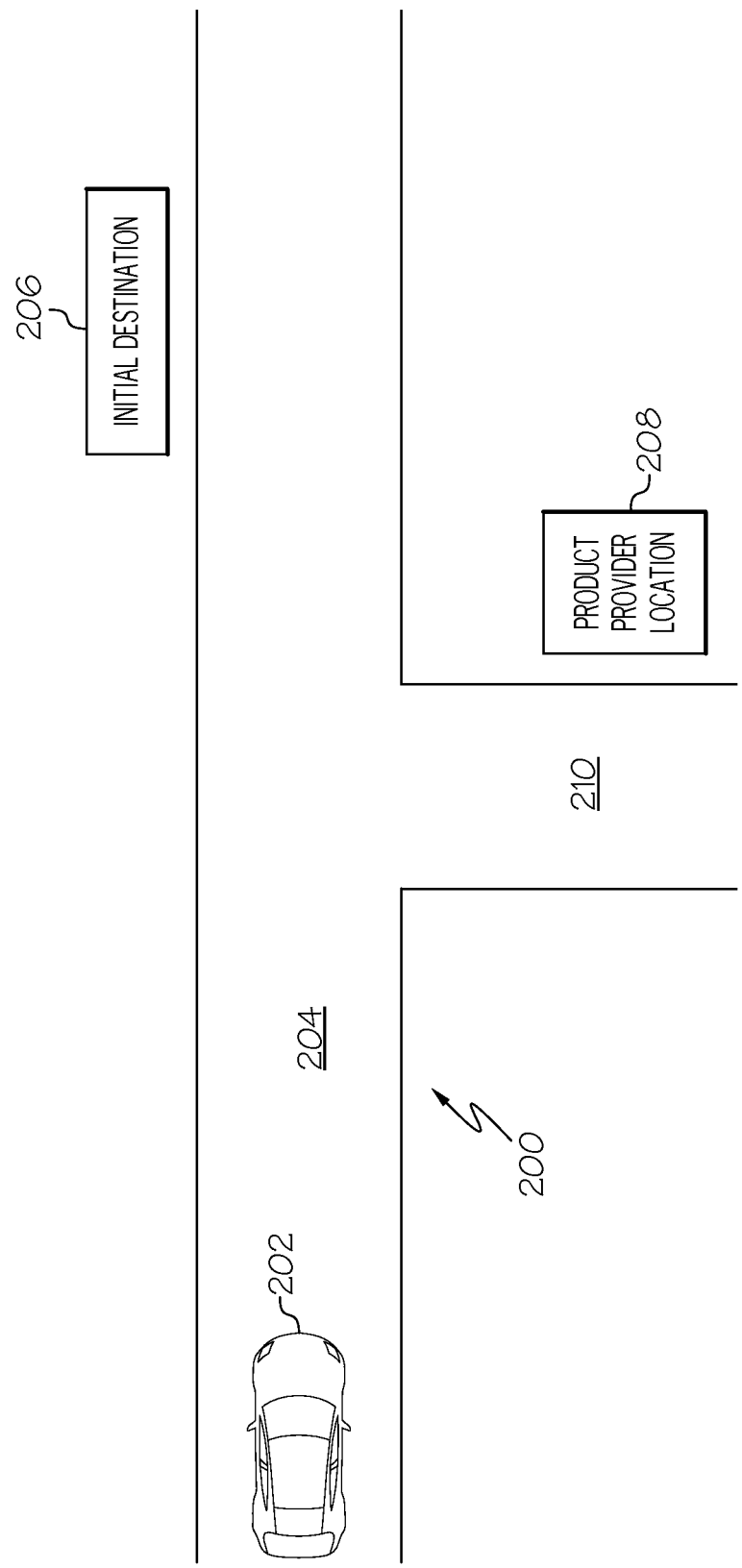
FIG. 2 illustrates an exemplary self-driving vehicle (SDV) operating on a roadway.

With reference now to FIG. 2, assume that an SDV is traveling along a roadway 200, which includes a roadway 204 and a side street 210. As depicted, the SDV 202 is traveling along roadway 204 towards an initial destination 206 according to an original planned route (which will take the SDV 202 to the initial destination 206). However, on the way to the initial destination, an on-board computer in the SDV 202 detects a scenario that requires the SDV 202 to alter its original planned route (to the initial destination 206) in order to autonomously drive the SDV 202 to a product provider location 208, which is depicted as being on side street 210.

The scenario that requires the SDV 202 to alter its route is based on one or more of 1) a current real-time location of the SDV 202; 2) the original planned route of the SDV 202; and/or a condition of one or more occupants of the SDV 202.

In one embodiment of the present invention, the condition of the one or more occupants of the SDV 202 that causes the SDV 202 to alter its route is a physiological condition, such as a medical injury, hunger, thirst, anxiety, etc. This physiological condition is detected by one or more physiological (e.g., biometric) sensors within a cabin of the SDV 202, as described herein.

Figure 3:
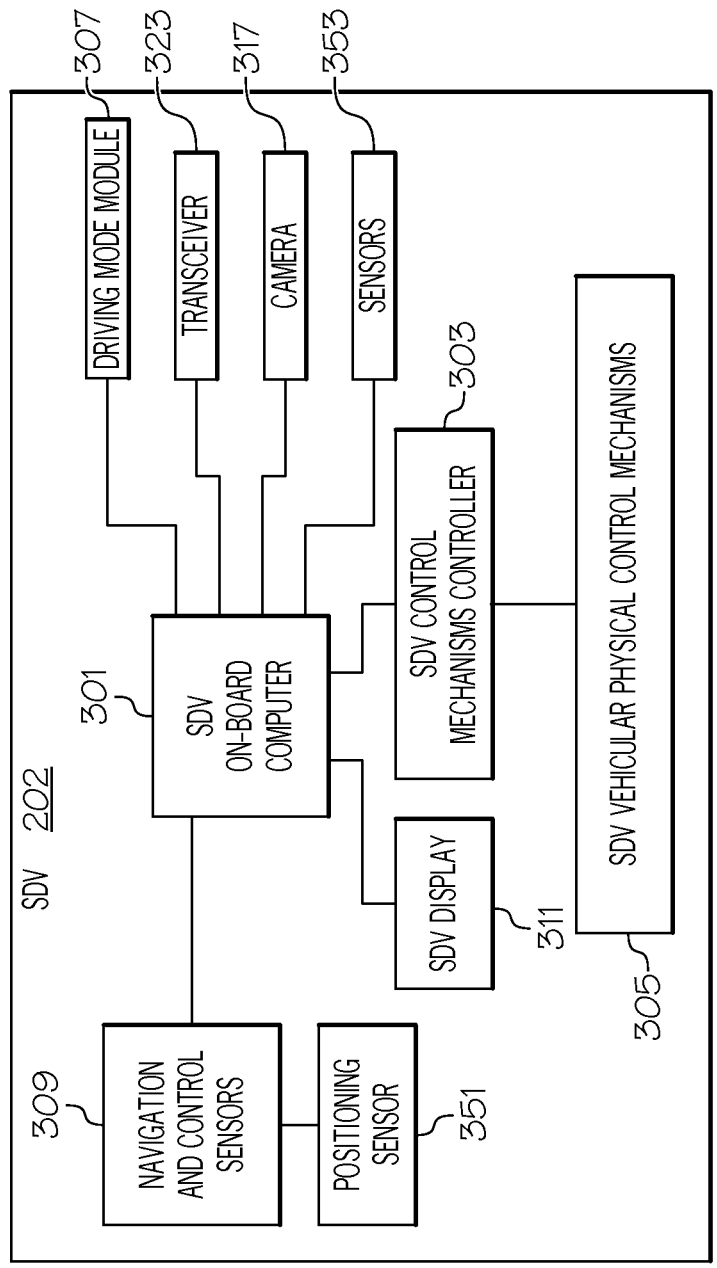
FIG. 3 depicts additional detail of control hardware within an SDV.

With reference now to FIG. 3, additional detail of electronic devices within the SDV 202 shown in FIG. 2 is presents. As shown in FIG. 3, SDV 202 has an SDV on-board computer 301 that controls operations of the SDV 202. According to directives from a driving mode module 307, SDV 202 can be selectively operated in manual mode or autonomous mode.

While in manual mode, SDV 202 operates as a traditional motor vehicle, in which a human driver controls the engine, steering mechanism, braking system, horn, signals, etc. found on a motor vehicle. These vehicle mechanisms may be operated in a "drive-by-wire" manner, in which inputs to an SDV control mechanisms controller 303 by the driver result in output signals that control the SDV vehicular physical control mechanisms 305 (e.g., the engine throttle, steering mechanisms, braking systems, turn signals, etc.).

While in autonomous mode, SDV 202 operates without the input of a human driver, such that the engine, steering mechanism, braking system, horn, signals, etc. are still controlled by the SDV control mechanisms controller 303, but now under the control of the SDV on-board computer 301. That is, by processing inputs taken from navigation and control sensors 309 (which may use inputs from a positioning sensor 351, analogous to positioning sensor 151 shown in FIG. 1, to indicate the current position of the SDV 202) and the driving mode module 307 indicating that the SDV 202 is to be controlled autonomously, then driver inputs are no longer needed.

As just mentioned, the SDV on-board computer 301 uses outputs from navigation and control sensors 309 to control the SDV 202. Navigation and control sensors 309 include hardware sensors that (1) determine the location of the SDV 202; (2) sense other cars and/or obstacles and/or physical structures around SDV 202; (3) measure the speed and direction of the SDV 202; and (4) provide any other inputs needed to safely control the movement of the SDV 202.

With respect to the feature of (1) determining the location of the SDV 202, this can be achieved through the use of a positioning system such as positioning system 151 shown in FIG. 1. Positioning system 151 may use a global positioning system (GPS), which uses space-based satellites that provide positioning signals that are triangulated by a GPS receiver to determine a 3-D geophysical position of the SDV 202. Positioning system 151 may also use, either alone or in conjunction with a GPS system, physical movement sensors such as accelerometers (which measure rates of changes to a vehicle in any direction), speedometers (which measure the instantaneous speed of a vehicle), air-flow meters (which measure the flow of air around a vehicle), etc. Such physical movement sensors may incorporate the use of semiconductor strain gauges, electromechanical gauges that take readings from drivetrain rotations, barometric sensors, etc.

With respect to the feature of (2) sensing other cars and/or obstacles and/or physical structures around SDV 202, the positioning system 151 may use radar or other electromagnetic energy that is emitted from an electromagnetic radiation transmitter (e.g., transceiver 323 shown in FIG. 3), bounced off a physical structure (e.g., another car), and then received by an electromagnetic radiation receiver (e.g., transceiver 323). By measuring the time it takes to receive back the emitted electromagnetic radiation, and/or evaluating a Doppler shift (i.e., a change in frequency to the electromagnetic radiation that is caused by the relative movement of the SDV 202 to objects being interrogated by the electromagnetic radiation) in the received electromagnetic radiation from when it was transmitted, the presence and location of other physical objects can be ascertained by the SDV on-board computer 301.

With respect to the feature of (3) measuring the speed and direction of the SDV 202, this can be accomplished by taking readings from an on-board speedometer (not depicted) on the SDV 202 and/or detecting movements to the steering mechanism (also not depicted) on the SDV 202 and/or the positioning system 151 discussed above.

With respect to the feature of (4) providing any other inputs needed to safely control the movement of the SDV 202, such inputs include, but are not limited to, control signals to activate a horn, turning indicators, flashing emergency lights, etc. on the SDV 202.

Figure 4:
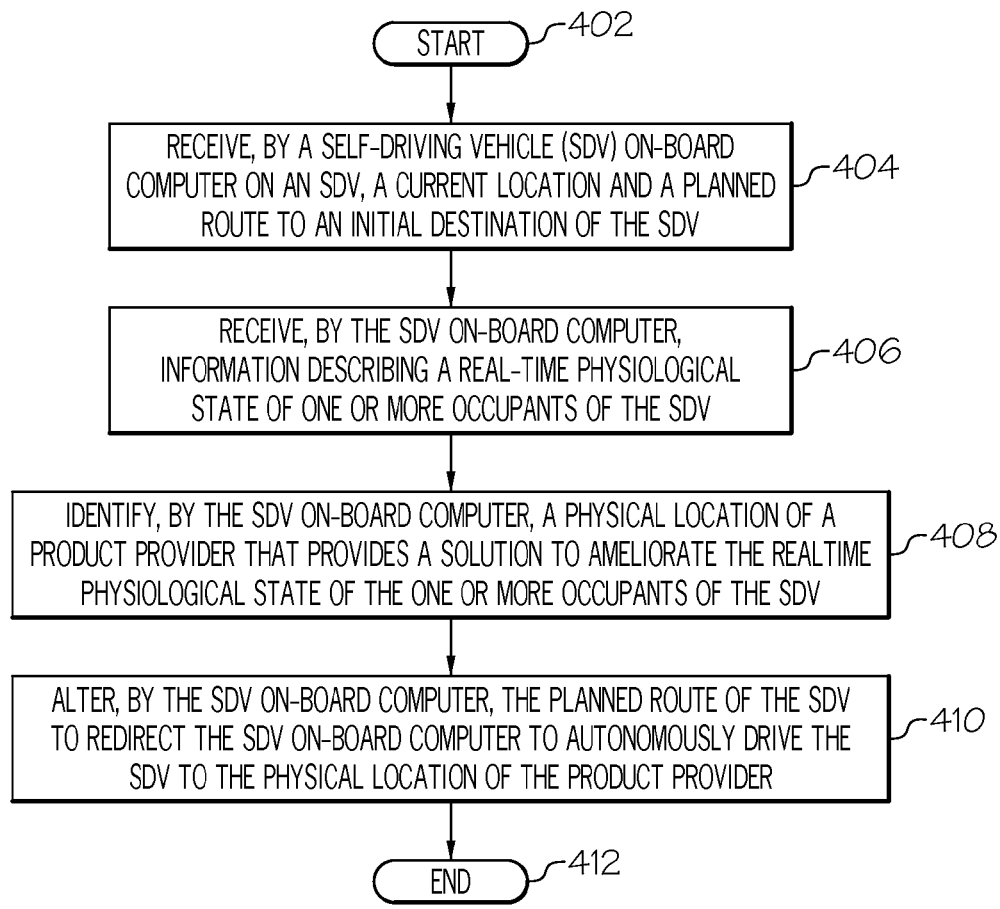
FIG. 4 is a high-level flow chart of one or more steps performed by one or more processors and/or other hardware to automatically alter a planned route of the SDV based on real-time physiological states of one or more occupants of an SDV.

With reference now to FIG. 4, a high-level flow chart of one or more steps performed by one or more processors and/or other hardware to automatically alter a planned route of an SDV based on real-time physiological states of one or more occupants of an SDV is presented.

After initiator block 402, a self-driving vehicle (SDV) on-board computer on an SDV (e.g., SDV on-board computer 301 shown within SDV 202 in FIG. 3) receives a current location and a planned route to an initial destination of the SDV, as described in block 404. The navigation and control sensors 309 using the positioning sensor 351 shown in FIG. 3 can determine the current location of the SDV 202. The planned route can be retrieved from memory within the SDV on-board computer 301. For example, the planned route can be entered manually by a person operating the SDV 202, or the planned route can be automatically configured by the SDV on-board computer 301 based on: (1) a starting location of the SDV 202; (2) a destination location for the SDV 202; (3) traits and features of the SDV 202; (4) current road conditions of roadways between the starting location and the destination location; and/or (5) current traffic conditions on the roadways between the starting location and the destination location.

The (1) a starting location of the SDV 202 is identified by the positioning sensor 351 shown in FIG. 3.

The (2) destination location for the SDV 202 may be manually input and/or configured by the SDV on-board computer 301. For example, a user may input into an interactive SDV display 311 that he/she wants to get gasoline for the SDV 202. The SDV on-board computer 301 will identify (from an on-board or remotely accessed database) a location of a nearest gas station as the destination location.

The (3) traits and features of the SDV 202 are defined in real-time or from a database. For example, in real time mechanical, tire, electrical, gas tank, etc. sensors determine the current condition of the SDV 202, including how much gas it has in the tank, the conditions of the tires (e.g., flat or inflated), the mechanical condition of the engine of the SDV 202 (e.g., is it running so rough that it is likely to stop running within the next three miles), etc. Alternatively, the traits and features of the SDV 202 can be derived from a database in a storage device, to describe the mileage range of the SDV 202, the maximum speed that SDV 202 can achieve, the safety rating of the SDV 202, etc.

The (4) current road conditions of roadways between the starting location and the destination location can be derived from sensors on the roadways between the starting location and the destination location. Such sensors may include weather sensors, pothole sensors, etc., which are either part of the roadways themselves, or else are reported by other SDVs traveling along the roadways between the starting location and the destination location.

The (5) current traffic conditions on the roadways between the starting location and the destination location can be also derived from sensors on the roadways between the starting location and the destination location. Such sensors may include pneumatic hose sensors that measure traffic density, electronic sensors that detect passing cars, traffic cameras aimed at the roadways, etc. Alternatively, such traffic reports can be generated by signals from other SDVs or other vehicles, reporting the speed of each vehicle. These speeds are then combined to create a traffic pattern report (e.g., by a third party server), which is then sent to the SDV 202.

As described in block 406, the SDV on-board computer also receives information describing a real-time physiological state of one or more occupants of the SDV. This physiological state may be purely physical, purely emotional/psychological, or a combination of physical and emotional/psychological states.

In one embodiment of the present invention, the real-time physiological state of one or more occupants of the SDV is detected by one or more biometric sensors (e.g., one or more of the sensors 353 shown in FIG. 3) that are within the cabin of the SDV 202 and/or that are affixed to the occupant(s). For example, a respiratory monitor may use a camera (e.g., camera 317 shown in FIG. 3) that detects chest movement (indicative of a person inhaling or exhaling) of an occupant. Alternatively, a respiratory monitor may be a strain gauge (not depicted in detail in the figures) that is worn by the occupant. The strain gauge measures a change in resistance to a ductile unit of wire within the strain gauge as the occupant's chest expands/contracts, indicative of a respiration cycle.

In one embodiment of the present invention, the camera (e.g., camera 317 shown in FIG. 3) captures other physical appearances of the occupant(s) for interpretation as one or more real-time physiological states of one or more of the occupant(s) of SDV 202. For example, rapid and/or erratic movement of an occupant's entire body may indicate a neurologic-based seizure (e.g., from epilepsy). Similarly, glistening of skin on the occupant's face captured by the camera may indicate over-heating of the occupant. Similarly, a severe grimace of the occupant's face may indicate a heart attack in progress or another internal organ problem. Similarly, rapid eye movement and/or trembling of the occupant's body captured by the camera may be indicative of the occupant experiencing a panic attack.

In one embodiment of the present invention, the real-time physiological state of the one or more occupants of the SDV is based on a user-selected input to an input device. For example, consider now FIG. 5, which depicts an exemplary graphical user interface (GUI) 501 that allows an occupant of SDV 202 to input his/her current and/or physiological state.

Figure 5:
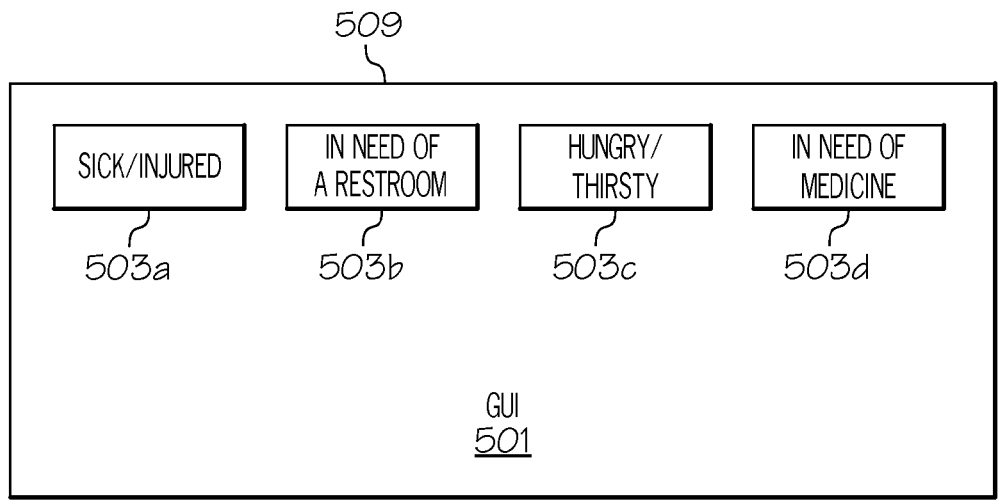
FIG. 5 depicts an exemplary graphical user interface (GUI) that allows an occupant of an SDV to input his/her current physiological state.

As shown in FIG. 5, GUI 501 is depicted on a display 509 (analogous to display 109 shown in FIG. 1) that is within a cabin of the SDV 202, on a smart phone or other computing device carried by the occupant of the SDV 202, etc. Displayed on GUI 501 are exemplary buttons 503*a*-503*d*. Assuming that display 509 is a touch screen capable of receiving touch inputs by the occupant(s), button 503*a* would be touched by the occupant(s) if he/she feels sick or has been injured (e.g., has cut himself/herself while riding in SDV 202). Similarly, if the occupant(s) needs to relieve himself (use a public restroom), he/she would touch button 503b. Similarly, if the occupant(s) is hungry or thirsty, he/she would touch button 503c. Similarly, if the occupant(s) feels the immediate need to take medication (e.g., a prescription item or an over-the-counter item), then he would touch button 503d.

In another embodiment, the touch buttons 503a-503d represent an anticipated physiological state of the occupant. For example, the occupant may feel fine at a current time, but the system knows that if the occupant does not ingest a glucose-rich beverage within the next 10 minutes, then he/she will be hypoglycemic in an hour. This knowledge may be based on a profile of the occupant. That is, a profile of the occupant may include medical records that state that if the occupant does not ingest a glucose-rich beverage every three hours, then he/she is likely to become hypoglycemic. Thus, the occupant does not need to activate any of the touch buttons 503a-503d in this embodiment, since the SDV on-board computer 301 on the SDV 202 will automatically drive the SDV to an appropriate vendor of glucose-rich beverages.

Note that none of the touch buttons 503a-503d describe where the occupant(s) wants to go. Rather, when a particular button from buttons 503a-503d is touched/activated, the SDV on-board computer 301 will correlate that input to an entry on a lookup table, which identifies specific product providers that can ameliorate the real-time condition of the occupant(s). For example, the product provider may provide a service (e.g., a physical therapist) or goods (e.g., medication) needed by the occupant(s).

In one embodiment of the present invention, the real-time physiological state of the one or more occupants of the SDV is received from a profile database that describes an on-going physiological condition of the one or more occupants of the SDV. That is, a profile database may contain physiological descriptors of an ongoing state of the occupant(s), such as diabetes, light sensitivity, etc. Such conditions are likely to always exist for the occupant(s). As such, if the SDV on-board computer 301 recognizes that the time of day is that which the occupant needs a beverage that is high in glucose, then the SDV 202 may be rerouted to a nearest beverage retailer that sells high-glucose beverages. Similarly, if a sensor on the SDV 202 is a camera that detects that (1) the sun is shining on the face of the occupant of the SDV 202, and (2) the occupant of the SDV 202 is not wearing sunglasses, then the SDV 202 may be rerouted to a nearest vendor of sunglasses. Alternately, if the occupant is light sensitive, the SDV 202 may be autonomously driven to an alternate route that is known to the system to provide more protection from the sun (e.g., a tunnel, under an elevated light rail support, a tree-lined road, etc.). Note that these examples are not to be construed as limiting to the present invention, and are used to clearly identify the process described and claimed in one or more embodiments of the present invention.

Returning now to FIG. 4, the SDV on-board computer identifies a physical location of a product provider that provides a solution to ameliorate the real-time physiological state of the one or more occupants of the SDV, as discussed above and represented by block 408.

As depicted in block 410, the SDV on-board computer then alters the planned route of the SDV (e.g., to the initial destination 206 shown in FIG. 2) to redirect the SDV on-board computer to autonomously drive the SDV to the physical location of the product provider (e.g., product provider 208 shown in FIG. 2).

The flow chart depicted in FIG. 4 ends at terminator block 412.

In one embodiment of the present invention, the decision to reroute the SDV 202 to a new product provider location is derived from one or more of the occupant(s) in the SDV 202 belonging to a cohort of similar persons. For example, assume that a particular occupant of an SDV has a characteristic (i.e., trait) found in other members of a cohort that share a particular physiological condition (e.g., being prone to anxiety). Assume further that historical data shows that when these cohort members have gone to a particular type of product provider (e.g., an herbal tea shop), they have reported a reduction in their anxiety level. As such, the system will anticipate that the SDV 202 needs to be directed to a nearest herbal tea shop if sensors, user inputs, or database descriptions of the occupant detect that this particular occupant is feeling anxious.

Thus in one embodiment of the present invention, one or more processors (e.g., a processor 103 within the SDV on-board computer 301 shown in FIG. 3) retrieve a physiological profile of the one or more occupants of the SDV (from user inputs, sensors, and/or a database). The processor(s) assign the one or more occupants of the SDV to a cohort of persons, where the one or more occupants of the SDV shares more than a predetermined quantity of traits with members of the cohort of persons. The processor(s) receive a rating for multiple product providers that ameliorate the real-time physiological states for members of the cohort of persons, where the multiple product providers are within a predefined spatial distance from the SDV, and then identify a highest rated product provider from the multiple product providers. For example, if there are three herbal tea vendors within 5 miles of SDV 202 in the example presented above, then the herbal tea vendor that has the highest feedback rating from members of the cohort is identified/selected. The SDV on-board computer then further alters the planned route of the SDV to redirect the SDV on-board computer to autonomously drive the SDV to a physical location of the highest rated product provider.

In one embodiment of the present invention, the selection of a particular vendor is based on how busy (e.g., how crowded with patrons/customers/patients/etc.) the vendor is in real-time (and thus how long a wait will be encountered at that particular vendor). The wait time can be transmitted by the vendor itself, or by other patrons of that vendor. Thus, in one embodiment of the present invention, one or more processors (e.g., within SDV on-board computer 301) receive a rating for multiple product providers that ameliorate the real-time physiological states for members of the cohort of persons (where the multiple product providers are within a predefined spatial distance from the SDV), identify a highest rated product provider from the multiple product providers, and then further alter, by the SDV on-board computer, the planned route of the SDV to redirect the SDV on-board computer to autonomously drive the SDV to a physical location of the highest rated product provider. However, the SDV on-board computer also receives a wait time message at the highest rated product provider, which describes a current wait time for receiving the product provided by the highest rated product provider (i.e., the solution to ameliorate the real-time physiological state of the one or more occupants of the SDV). In response to determining that the current wait time exceeds the predetermined level, the SDV on-board computer further alters the planned route of the SDV to redirect the SDV on-board computer to retrieve a physical location of a second highest rated product provider from the multiple product providers, and to autonomously drive the SDV to the second highest rated product provider from the multiple product providers.

Similarly, if the product provider location 208 shown in FIG. 2 is a public restroom that is needed by the occupant of the SDV 202 but that is currently occupied, locked, or otherwise not currently available for use, the system will redirect the SDV 202 to the next nearest public restroom that is currently available for use.

In an embodiment of the present invention, a weighted voting system is used to weight various variables used in making the decisions regarding whether to redirect the SDV 202. Such inputs may include a level of anxiety or other physiological issues being experienced by various occupants of an SDV, which provides a weighting for such factors. For example, if all occupants of an SDV feel moderately uncomfortable due to needing to eat, then a certain weighted sum will be determined, which may be enough to cause the SDV to be redirected to a nearest restaurant. Alternatively, if only one of five occupants in the SDV are hungry, then the SDV will continue on to the original destination. The physiological state level inputs (describing one or more real-time physiological states of occupants of the SDV) are (I1, I2, ..., IN), where "N" denotes the total number of inputs. An input's weight (w) is how significant the input level is (i.e., how significant (weighted) the input is). A quota (q) is the minimum number of votes (e.g., weighted inputs from the occupants) required to "pass a motion", which in this case refers to a decision made to alter the route of the SDV.

Thus, in one embodiment of the present invention, multiple occupants are within the SDV, and one or more processors receive a weighted physiological state descriptor for each of the multiple occupants within the SDV. The processor(s) determine a weighted average physiological state descriptor for the multiple occupants within the SDV. The control mechanisms controller then alters where the SDV goes based on the weighted average physiological state descriptor for the multiple occupants within the SDV.

In one or more embodiments, the present invention is implemented in a cloud environment. It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
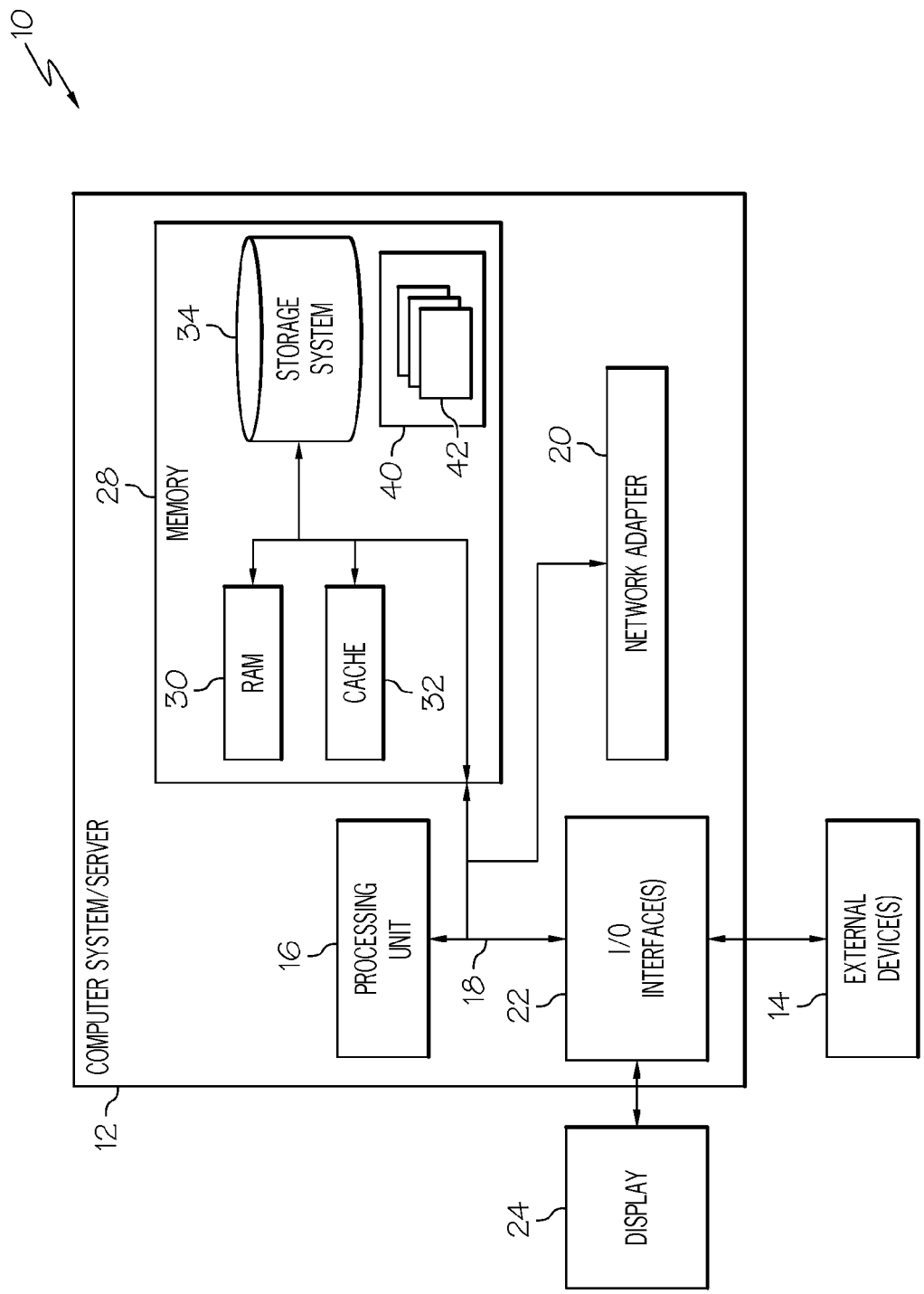
FIG. 6 depicts a cloud computing node according to an embodiment of the present disclosure.

Referring now to FIG. 6, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 7:
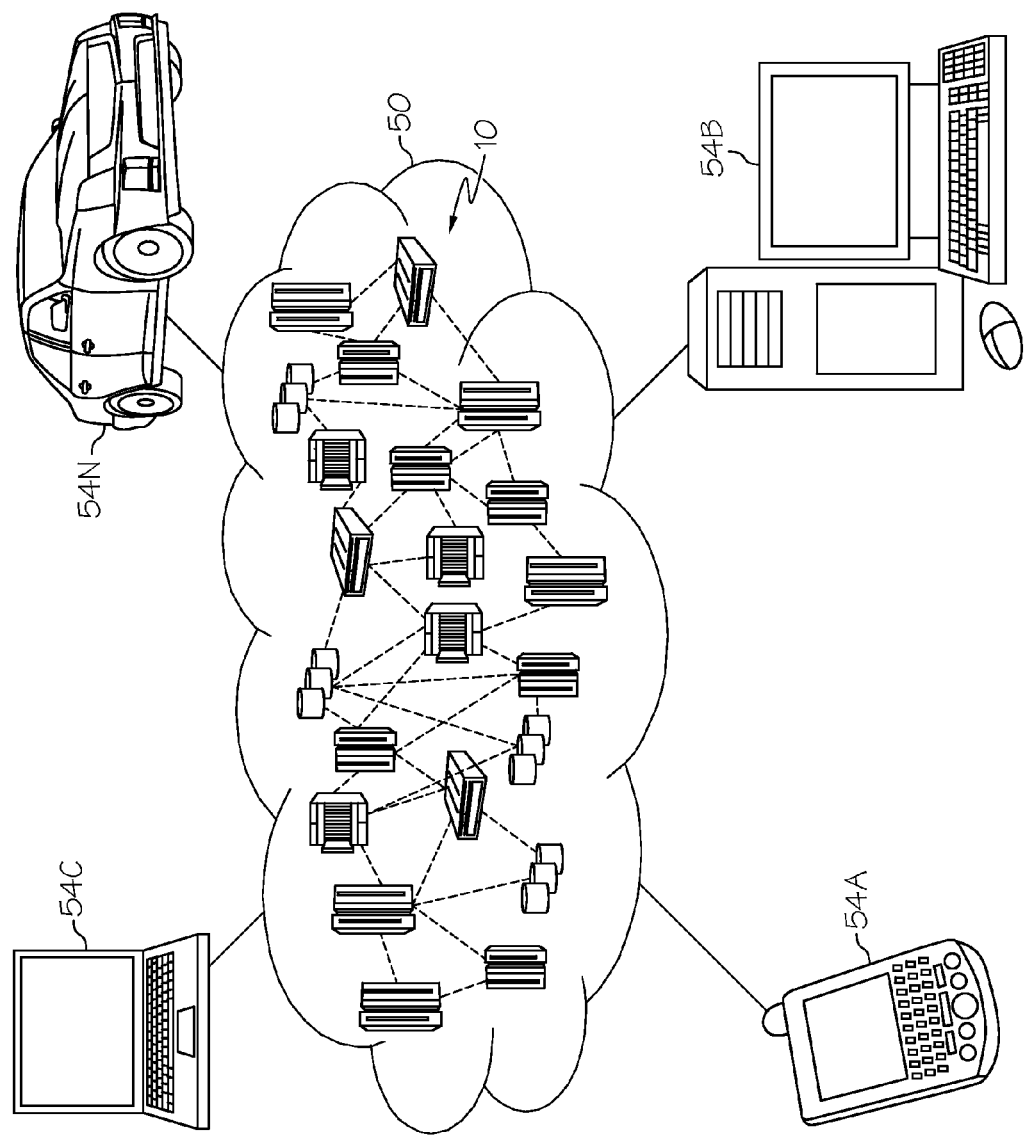
FIG. 7 depicts a cloud computing environment according to an embodiment of the present disclosure.

Referring now to FIG. 7, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone MA, desktop computer MB, laptop computer MC, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 7 are intended to be illustrative only and that computing nodes 10 and cloud computing environment 50 can communicate with any type of computerized device over any type of network and/or network addressable connection (e.g., using a web browser).

Figure 8:
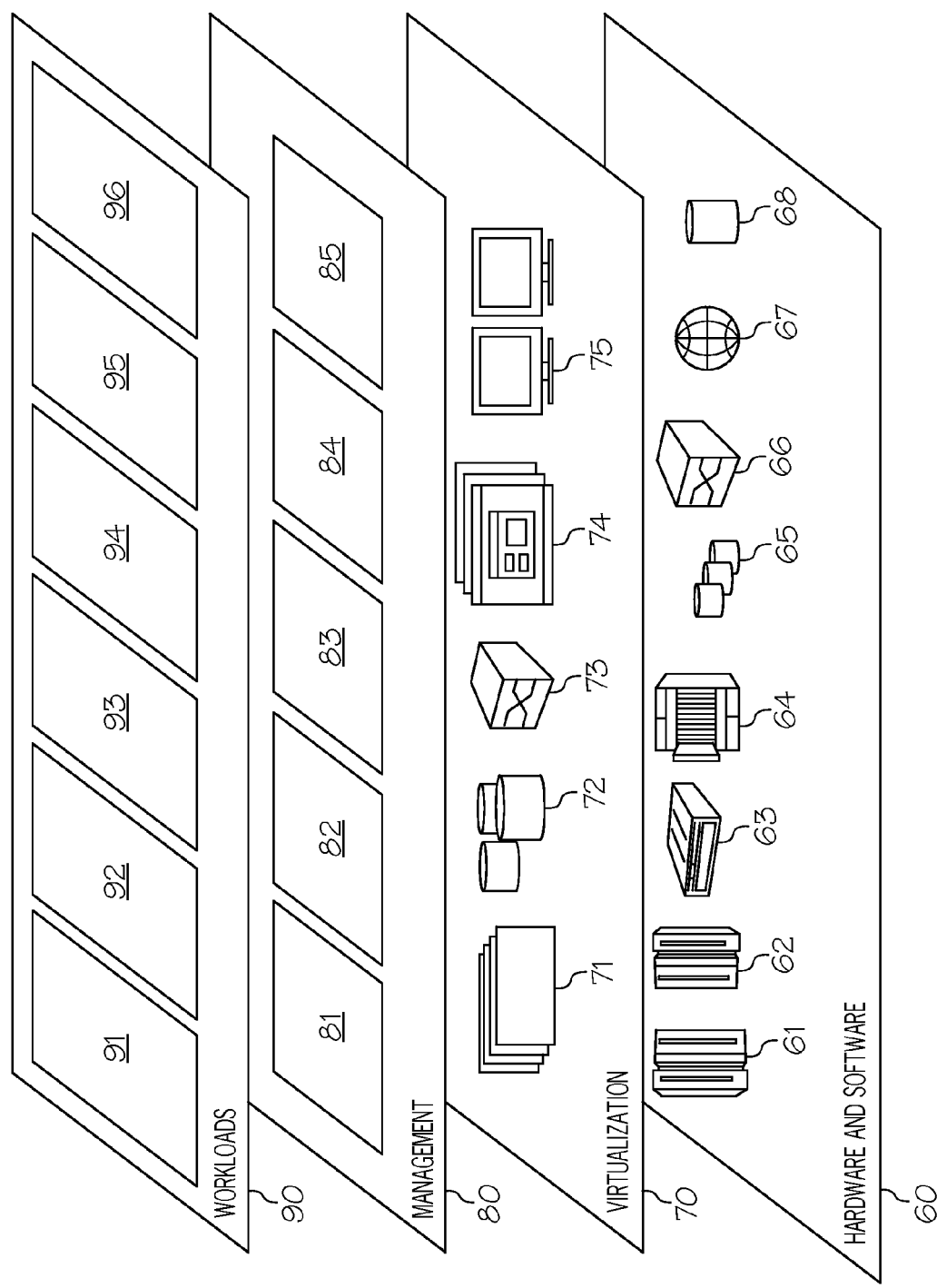
FIG. 8 depicts abstraction model layers according to an embodiment of the present disclosure.

Referring now to FIG. 8, a set of functional abstraction layers provided by cloud computing environment 50 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and self-driving vehicle control processing 96 (for adjusting a route to be followed by the SDV as described herein).

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the present invention in the form disclosed. Many modifications and variations will be apparent to those of ordinary skill in the art without departing from the scope and spirit of the present invention. The embodiment was chosen and described in order to best explain the principles of the present invention and the practical application, and to enable others of ordinary skill in the art to understand the present invention for various embodiments with various modifications as are suited to the particular use contemplated.

Any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the present invention of the present application in detail and by reference to illustrative embodiments thereof, it will be apparent that modifications and variations are possible without departing from the scope of the present invention defined in the appended claims.

What is claimed is:

1. A computer-implemented method for redirecting a self-driving vehicle (SDV) to a physical location of a product provider, the computer-implemented method comprising:

receiving, by a self-driving vehicle (SDV) on-board computer on an SDV, a current location and a planned route to an initial destination of the SDV;

receiving, by the SDV on-board computer, information describing a real-time physiological state of one or more occupants of the SDV;

identifying, by the SDV on-board computer, a physical location of a product provider that provides a solution to ameliorate the real-time physiological state of the one or more occupants of the SDV;

altering, by the SDV on-board computer, the planned route of the SDV to redirect the SDV on-board computer to autonomously drive the SDV to the physical location of the product provider;

retrieving, by one or more processors, a physiological profile of the one or more occupants of the SDV;

assigning, by one or more processors, the one or more occupants of the SDV to a cohort of persons, wherein the one or more occupants of the SDV shares more than a predetermined quantity of traits with members of the cohort of persons;

receiving, by one or more processors, a rating for multiple product providers that ameliorate the real-time physiological states for members of the cohort of persons, wherein the multiple product providers are within a predefined spatial distance from the SDV;

identifying, by one or more processors, a highest rated product provider from the multiple product providers; and further altering, by the SDV on-board computer, the planned route of the SDV to redirect the SDV on-board computer to autonomously drive the SDV to a physical location of the highest rated product provider.

2. The computer-implemented method of claim 1, further comprising:
receiving, by the SDV on-board computer, the real-time physiological state of the one or more occupants of the SDV from a biometric sensor that monitors the one or more occupants.

3. The computer-implemented method of claim 1, further comprising:
receiving, by the SDV on-board computer, a visual image from a camera in a cabin of the SDV, wherein the visual image depicts the one or more occupants; and
interpreting, by one or more processors, the visual image to generate the real-time physiological state of the one or more occupants of the SDV.

4. The computer-implemented method of claim 1, further comprising:
receiving, by the SDV on-board computer, the real-time physiological state of the one or more occupants of the SDV from a user-selected input to an input device.

5. The computer-implemented method of claim 1, further comprising:
receiving, by the SDV on-board computer, the real-time physiological state of the one or more occupants of the SDV from a profile database that describes an on-going physiological condition of the one or more occupants of the SDV.

6. The computer-implemented method of claim 1, further comprising:
receiving, by one or more processors, a rating for multiple product providers that ameliorate the real-time physiological states for members of a cohort of persons, wherein the multiple product providers are within a predefined spatial distance from the SDV;
identifying, by one or more processors, a highest rated product provider from the multiple product providers; and
further altering, by the SDV on-board computer, the planned route of the SDV to redirect the SDV on-board computer to autonomously drive the SDV to a physical location of the highest rated product provider;
receiving, by the SDV on-board computer, a wait time message at the highest rated product provider, wherein the wait time message describes a current wait time for receiving the solution to ameliorate the real-time physiological states of the one or more occupants of the SDV at the highest rated product provider;
determining, by one or more processors, that the current wait time exceeds a predetermined level; and
in response to determining that the current wait time exceeds the predetermined level, further altering, by the SDV on-board computer, the planned route of the SDV to redirect the SDV on-board computer retrieve a physical location of a second highest rated product provider from the multiple product providers, and to autonomously drive the SDV to the second highest rated product provider from the multiple product providers.

7. A computer program product for redirecting a self-driving vehicle (SDV) to a physical location of a product provider, the computer program product comprising a non-transitory computer readable storage medium having program code embodied therewith, the program code readable and executable by a processor to perform a method comprising:
receiving a current location and a planned route to an initial destination of a self-driving vehicle (SDV);
receiving information describing real-time physiological states of one or more occupants of the SDV;
identifying a physical location of a product provider that provides a solution to ameliorate the real-time physiological states of the one or more occupants of the SDV;
altering the planned route of the SDV to redirect the SDV on-board computer to autonomously drive the SDV to the physical location of the product provider;
receiving a rating for multiple product providers that ameliorate the real-time physiological states for members of the cohort of persons, wherein the multiple product providers are within a predefined spatial distance from the SDV;
receiving a wait time message at a highest rated product provider, wherein the wait time message describes a current wait time for receiving the solution to ameliorate the real-time physiological states of the one or more occupants of the SDV at the highest rated product provider;
determining that the current wait time exceeds a predetermined level; and
in response to determining that the current wait time exceeds the predetermined level, further altering the planned route of the SDV to redirect the SDV on-board computer to retrieve a physical location of a second highest rated product provider from the multiple product providers, and to autonomously drive the SDV to the second highest rated product provider from the multiple product providers.

8. The computer program product of claim 7, wherein the method further comprises:
receiving the real-time physiological states of the one or more occupants of the SDV from a biometric sensor that monitors the one or more occupants.

9. The computer program product of claim 7, wherein the method further comprises:
receiving a visual image from a camera in a cabin of the SDV, wherein the visual image depicts the one or more occupants; and
interpreting the visual image to generate the real-time physiological states of the one or more occupants of the SDV.

10. The computer program product of claim 7, wherein the method further comprises:
receiving the real-time physiological states of the one or more occupants of the SDV from a user-selected input to an input device.

11. The computer program product of claim 7, wherein the method further comprises:
receiving the real-time physiological states of the one or more occupants of the SDV from a profile database that describes an on-going physiological condition of the one or more occupants of the SDV.

12. The computer program product of claim 7, wherein the method further comprises:
retrieving a physiological profile of the one or more occupants of the SDV;
assigning the one or more occupants of the SDV to a cohort of persons, wherein the one or more occupants of the SDV shares more than a predetermined quantity of traits with members of the cohort of persons;
receiving a rating for multiple product providers that ameliorate the real-time physiological states for members of the cohort of persons, wherein the multiple product providers are within a predefined spatial distance from the SDV;

identifying a highest rated product provider from the multiple product providers; and further altering the planned route of the SDV to redirect the SDV on-board computer to autonomously drive the SDV to a physical location of the highest rated product provider.

13. A computer system comprising:

a processor, a computer readable memory, and a non-transitory computer readable storage medium;

first program instructions to receive a current location and a planned route to an initial destination of a self-driving vehicle (SDV);

second program instructions to receive information describing a real-time physiological states of one or more occupants of the SDV;

third program instructions to identify a physical location of a product provider that provides a solution to ameliorate the real-time physiological states of the one or more occupants of the SDV;

fourth program instructions to alter the planned route of the SDV to redirect the SDV on-board computer to autonomously drive the SDV to the physical location of the product provider;

fifth program instructions to retrieve a physiological profile of the one or more occupants of the SDV;

sixth program instructions to assign the one or more occupants of the SDV to a cohort of persons, wherein the one or more occupants of the SDV shares more than a predetermined quantity of traits with members of the cohort of persons;

seventh program instructions to receive a rating for multiple product providers that ameliorate the real-time physiological states for members of the cohort of persons, wherein the multiple product providers are within a predefined spatial distance from the SDV;

eighth program instructions to identify a highest rated product provider from the multiple product providers;

ninth program instructions to further alter the planned route of the SDV to redirect the SDV on-board computer to autonomously drive the SDV to a physical location of the highest rated product provider;

tenth program instructions to receive a wait time message at the highest rated product provider, wherein the wait time message describes a current wait time for receiving the solution to ameliorate the real-time physiological states of the one or more occupants of the SDV at the highest rated product provider;

eleventh program instructions to determine that the current wait time exceeds a predetermined level; and twelfth program instructions to, in response to determining that the current wait time exceeds the predetermined level, further alter the planned route of the SDV to redirect the SDV on-board computer to retrieve a physical location of a second highest rated product provider from the multiple product providers, and to autonomously drive the SDV to the second highest rated product provider from the multiple product providers; and wherein the first, second, third, fourth, fifth, sixth, seventh, eighth, ninth, tenth, eleventh, and twelfth program instructions are stored on the non-transitory computer readable storage medium for execution by one or more processors via the computer readable memory.

14. The computer system of claim 13, further comprising:

thirteenth program instructions to receive the real-time physiological states of the one or more occupants of the SDV from a biometric sensor that monitors the one or more occupants; and wherein the thirteenth program instructions are stored on the non-transitory computer readable storage medium for execution by one or more processors via the computer readable memory.

15. The computer system of claim 13, further comprising:

thirteenth program instructions to receive a visual image from a camera in a cabin of the SDV, wherein the visual image depicts the one or more occupants; and fourteenth program instructions to interpret the visual image to generate the real-time physiological states of the one or more occupants of the SDV; and wherein the thirteenth and fourteenth program instructions are stored on the non-transitory computer readable storage medium for execution by one or more processors via the computer readable memory.

16. The computer system of claim 13, further comprising:

thirteenth program instructions to receive the real-time physiological states of the one or more occupants of the SDV from a user-selected input to an input device; and wherein the thirteenth program instructions are stored on the non-transitory computer readable storage medium for execution by one or more processors via the computer readable memory.

17. The computer system of claim 13, further comprising:

thirteenth program instructions to receive the real-time physiological states of the one or more occupants of the SDV from a profile database that describes an on-going physiological condition of the one or more occupants of the SDV; and wherein the thirteenth program instructions are stored on the non-transitory computer readable storage medium for execution by one or more processors via the computer readable memory.

* * * * *